United States Patent [19]

Rosencwaig et al.

[11] Patent Number: 4,636,088

[45] Date of Patent: * Jan. 13, 1987

[54] METHOD AND APPARATUS FOR EVALUATING SURFACE CONDITIONS OF A SAMPLE

[75] Inventors: Allan Rosencwaig, Danville; Walter L. Smith, Livermore, both of Calif.

[73] Assignee: Therma-Wave, Inc., Fremont, Calif.

[*] Notice: The portion of the term of this patent subsequent to Apr. 1, 2003 has been disclaimed.

[21] Appl. No.: 612,076

[22] Filed: May 21, 1984

[51] Int. Cl.⁴ .................... G01N 21/41; G01N 25/00
[52] U.S. Cl. .................................... 374/5; 356/357; 356/445; 374/57
[58] Field of Search ................ 374/121, 45, 55, 117, 374/57, 6, 7, 5; 356/357

[56] References Cited

U.S. PATENT DOCUMENTS

| | | | |
|---|---|---|---|
| 3,462,602 | 8/1969 | Apple | 250/338 |
| 3,930,730 | 1/1976 | Laurens et al. | 356/357 |
| 4,243,327 | 1/1981 | Frosch et al. | 374/43 X |
| 4,255,971 | 3/1981 | Rosencwaig | 374/57 X |
| 4,358,201 | 11/1982 | Makosch | 356/358 X |
| 4,446,719 | 5/1984 | Lambert | 250/341 X |
| 4,455,741 | 6/1984 | Kolodner | 374/161 X |
| 4,468,136 | 8/1984 | Murphy et al. | 374/57 X |
| 4,579,463 | 4/1986 | Rosencwaig | 374/57 |

OTHER PUBLICATIONS

"Non-Destructive Interferometric Detection of Unbonded Layers", by P. Cielo, pp. 231-248, reprint of Optics & Lasers in Engineering, 1/14/84.

"Thermal & Plasma Wave Depth Profiling in Silicon", (Opsal et al) pp. 498-500, Applied Phys. Letters 47(5), 1/9/85.

"Ion Implant Monitoring with Thermal Wave Technology", Smith et al., pp. 584-586, Applied Phys. Letters 47(6), 15 Sep. '85.

"Thermal Wave Detection & Thin-Film Thickness Measurements with Laser Beam Detection", Jon Opsal, Rosencwaig, et al, Applied Optics, 10/15/83, vol. 22, No. 20, pp. 3169-3176.

Primary Examiner—Daniel M. Yasich
Attorney, Agent, or Firm—Limbach, Limbach & Sutton

[57] ABSTRACT

An apparatus and method is disclosed for evaluating surface conditions on a sample. The system is particularly suited for detecting thin residues encountered in semiconductor lithographic and etching processes. The system is also capable of measuring ion implanted dopant concentrations prior to annealing. The apparatus includes an intensity modulated laser beam which is focused on the surface of the sample to generate periodic heating. A second light beam is focused onto the periodically heated area of the sample in a manner such that it is reflected to a detector. The intensity changes in the probe beam, resulting from the temperature induced changes of reflectivity at the surface of the sample, are measured and evaluated to determine the absence or presence of residues, or to measure the concentrations of ion implanted dopants.

27 Claims, 5 Drawing Figures

METHOD AND APPARATUS FOR EVALUATING SURFACE CONDITIONS OF A SAMPLE

DESCRIPTION

1. Technical Field

The subject invention relates to a new and improved apparatus and method for evaluating surface conditions of a sample. The subject invention is particularly suited for applications in the semiconductor industry. For example, the subject invention is capable of detecting very small amounts of residues on the surface of a sample. In addition, the subject invention is capable of measuring ion implanted dopant concentrations adjacent the sample surface, prior to annealing.

2. Background Art

There has been a great amount of interest in developing techniques for accurately analyzing surface conditions of a sample. This interest is particularly acute in the semiconductor industry where there is a need for equipment, which is highly accurate and can evaluate surface layers that are extremely thin.

One specific situation where this need has not been solved relates to the detection of residues. More specifically, during the etching and lithographic processes used in fabricating integrated circuits, very thin residue layers are left behind which are almost impossible to detect, yet can lead to an early failure of the circuit.

Figure 1:
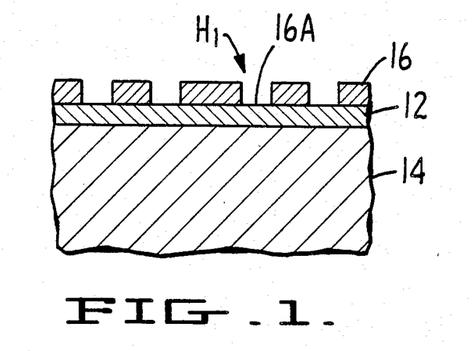
FIGS. 1 and 2 are cross-sectional views illustrating the lithographic and etching process of a typical integrated circuit and the problems associated therewith.
Figure 2:
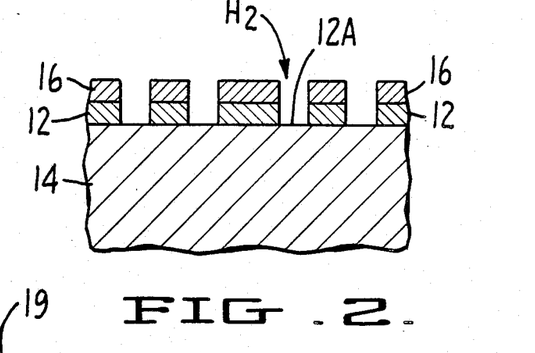

Referring to FIGS. 1 and 2, there is illustrated the typical steps associated with the fabrication of a semiconductor. More specifically, and as shown in FIG. 1, a layer 12 of an oxide is deposited on a silicon substrate 14. The next step in the preparation of a semiconductor is to etch a pattern in the oxide through a lithographic and etching process. For example, a layer of photoresist material 16 is applied to the upper surface of the oxide. A mask is placed over the photoresist material and it is then exposed to light. The nonexposed portions are then removed to produce the structure that is illustrated in FIG. 1. The thickness dimensions have been exaggerated for purposes of clarity.

Ideally, the latter structure is then "etched" in a step wherein portions of the oxide layer are removed in areas where the photoresist has been removed. A typical structure which is produced after the etching step is illustrated in FIG. 2.

Unfortunately, mass production fabrication techniques do not always yield perfect devices. For example, the step of removing portions of the photoresist is often less than complete. In contrast, residues may remain as indicated at 16A in FIG. 1. Where residues remain, the step of removing portions of the oxide layer will be inhibited. Even where the photoresist has been properly removed, the etching of the oxide layer is also prone to failures. As illustrated in FIG. 2, residues of the oxide 12A may remain. In either case, the integrated circuit which is manufactured from these imperfect structures will either be inoperative or prone to early failure.

To date, the industry has not come up with any good methods for detecting the residues. In most manufacturing settings, the integrated circuits are subject to optical microscopic examination by human operators. As can be appreciated, this can be very time consuming and inefficient. Furthermore, the thickness of residues which can adversely affect the fabrication of the integrated circuits are so thin as to be nearly invisible, even when inspected through an microscope.

Another technique used involves the principle of fluorescence. In this technique, the photoresist is illuminated with U.V. radiation and the resultant fluoresence is observed. In some cases, residues of the photoresist material can be detected. However, similar to the standard visual inspection, the fluorescent method only gives gross indications of the success or failure of the removal or etching steps of the photoresist material. In addition, the fluorescent technique is applicable only to photoresist residues and not to the oxide or other residues.

Another problem with these prior art detection techniques is that they are not very precise or accurate. More specifically, residues which remain are often trapped at the bottom of a "hole" or "contact" which has been etched, as indicated in cross-section FIG. 2. In order to detect these residues, a system which can be accurately focused is needed.

Figure 3:
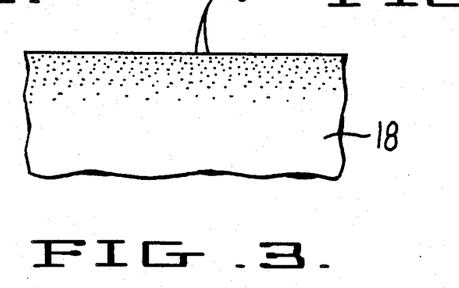
FIG. 3 is a cross-sectional view of an integrated circuit illustrating the implantation of dopant ions.

There are other times during the fabrication of an integrated circuit when it would be desirable to evaluate the surface condition of the sample. For example, semiconductive properties are often imparted to a silicon subtrate by implanting dopants having different electrical conductivites. Referring to FIG. 3, there is illustrated a silicon substrate 18 having dopant ions 19 implanted therein, adjacent the upper surface thereof.

In a typical implantation process, an ion beam is rastered over the surface of the sample. Some of the ions in the beam which bombard the sample are introduced into the lattice structure of the silicon. The concentration of the dopant ions in the sample is related to the length of time which the beam is focused on any point on the surface of the sample. The depth to which the ions penetrate is related to the voltage on the ion beam. However, even at maximum voltage, the depth to which the ions penetrate is relatively small such that the ion concentrations of interest are substantially at the upper surface of the sample.

The ions which are incorporated into the surface of the silicon are located at interstitial sites and physically disrupt the lattice structure of the material. In this state, the material will not exhibit the desired semiconductive properties. In order to overcome this problem, it is necessary to "activate the dopant" in a subsequent fabrication step. The dopant is activated through an annealing process. In the annealing process, the material is heated in a manner to permit the lattice to reform, enabling the ions to move from the interstitial sites to substitutional sites. In this process, the dopant ions are substituted for silicon at various points in the lattice. This annealing step functions to remove defects in the lattice and free the electrons of the dopant ions for conduction of current.

Once the annealing step has been performed, the dopant levels which have been implanted usually can be measured by known electrical resistivity methods. As can be appreciated, since the doped silicon is now at least partially conductive, indications of the dopant characteristics can be obtained simply by measuring electrical parameters. In a common arrangement, where boron ions are implanted into silicon, the present electrical testing procedures are able to detect concentrations as low as $10^{13}$ ions/cm$^2$. Unfortunately, it would be desirable to detect concentrations as low as $10^{11}$ ions/cm$^2$.

Furthermore, and more importantly, the prior art electrical technique has the additional shortcoming of being unable to detect ion concentrations prior to annealing. As set forth above, prior to annealing, the electrons of the dopant ions in the sample are locked at interstitial sites in the lattice structure. Accordingly, no information can be obtained by electrical measurement techniques. In fact, there is presently no method for evaluating the ion implant dopant concentrations directly on the sample prior to annealing. Such evaluation at this early stage is highly desirable since it can give information about success or failure of the implantation step prior to the expense of annealing. In addition, such information can be invaluable in designing fabrication steps to improve and alter the characteristics of an integrated circuit.

Accordingly, it is an object of the subject invention to provide a new and improved apparatus and method for evaluating the surface conditions of a sample.

It is another object of the subject invention to provide a new and improved apparatus and method for evaluating surface conditions based on the principles of reflectivity.

It is a further object of the subject invention to provide a method and apparatus for evaluating extremely thin surface layer characteristics of less than 100 Angstroms.

It is still a further object of the subject invention to provide a new and improved apparatus for evaluating surface conditions which can be accurately focused.

It is still another object of the subject invention to provide a new and improved apparatus and method for detecting residues on a sample.

It is still a further object of the subject invention to provide a new and improved method and apparatus for evaluating the dopant concentrations adjacent the surface of the sample prior to annealing.

It is still another object of the subject invention to provide a new method and apparatus for measuring dopant concentrations which is more sensitive than the equipment available heretofore.

SUMMARY OF THE INVENTION

In accordance with these and many other objects, the subject invention provides for a new and improved method and apparatus for evaluating the surface conditions of a sample. The method and apparatus is based on the principle that the change in optical reflectivity of a sample as it is heated will be different, depending upon varying surface conditions. It has been known that optical reflectivity is dependent to some extent on temperature. This dependence is defined by the following equation:

$$R_T = R_o + (\delta R/\delta T)(\Delta T) \quad (1)$$

In this equation $R_o$ represents the reflectivity at a set temperature and the second term in the equation gives the change in reflectivity resulting from the change in the temperature of the sample surface. The term $(\delta R/\delta T)$ is the temperature coefficient of reflectivity which represents the rate of change in reflectivity with respect to the change in temperature. The first term, $R_o$, is at least four orders of magnitude greater than the second term for temperature changes $\Delta T$ of less than 100 degrees. Furthermore, the noise level associated with $\sqrt{R_o}$, as measured with a photodetector, is on the order of $R_0$. The latter value is still 100 times greater than the second term of the equation which makes measurement of the second term quite difficult. In absolute terms, the value of the ratio $(\delta R/\delta T)(\Delta T)/R_o$ is on the order of $10^{-4}$ to $10^{-5}$ and therefore, has not been used as a measurement parameter.

In accordance with the subject invention, this difficulty is overcome by modulating the heating source. Periodic changes in reflectivity, which are occurring at the frequency of the modulation beam, are then monitored. This information can be processed by passing the signal through narrow bandwidth filters. The result is that the only periodic reflectivity signal $\Delta R_T$, resulting from the periodic temperature variations $\Delta T$ is measured rather than the absolute reflectivity $R_T$.

The periodic reflectivity signal $\Delta R_T$ is defined by the following equation:

$$\Delta R_T = (\delta R/\delta T)(\Delta T) \quad (2)$$

As seen from the above equation, the periodic reflectivity signal $\Delta R_T$ is dependent on the temperature coefficient of reflectivity $(\delta R/\delta T)$ times the periodic surface temperature $(\Delta T)$. Where a surface layer is present, the relative effect of the latter two variables on the change in periodic reflectivity $\Delta R_T$ is dependent, in part, upon the thickness of that surface layer. More specifically, where the residue layer (or perturbed surface layer) is less than 100 Angstroms thick, the effect on the periodic reflectivity signal $\Delta R_T$, due to the presence of the surface layer, is primarily a result of the change in the temperature coefficient of reflectivity $(\delta R/\delta T)$. This is so because such a thin layer will have a neglible effect on the periodic surface temperature $\Delta T$.

The change in the temperature coefficient of reflectivity $(\delta R/\delta T)$ is measurable even for very thin layers. In practice, it has been found that a change in the temperature coefficient of reflectivity can be measured when the layer of interest is as thin as 5 Angstroms. This sensitivity is based on the principle that a "clean" or undoped substrate will have a particular coefficient of reflectivity. The presence of dopants or a residue layer having a thickness as little as 5 Angstroms will nonetheless alter the temperature coefficient of reflectivity in a measurable manner. The ability to analyze such thin layers is based on the fact that reflection of an electromagnetic beam occurs right at the surface of the sample and any residues or dopants at or near the surface boundary will affect the temperature coefficient of reflectivity.

Where the residue layer or perturbed dopant region is greater than 100 Angstroms thick, the thermal parameters of the surface layer will also have an effect on the periodic reflectivity signal $\Delta R_T$. As can be appreciated, the layer of interest will have thermal characteristics that are different from the underlying substrate. When this layer is extremely thin, the thermal characteristics are defined almost entirely by the underlying substrate. However, when the thickness of the layer of interest is increased, its effect on the thermal characteristics of the system will be evident through its effect on the periodic surface temperature $\Delta T$.

Where there is a periodic heat source, the changing surface temperatures are a result of and defined by underlying thermal waves. A discussion of the generation of thermal waves by focusing an intensity modulated heat source on a sample can be found in applicant's prior U.S. Pat. No. 4,255,971, assigned to the same assignee as the subject invention and incorporated herein by reference. The relationship between the change in reflectivity and the generation of thermal waves provides an entirely new mechanism for measuring thermal waves in a sample. The measurement of thermal waves based on the change in reflectivity of a sample is disclosed in copending application, Ser. No. 612,075, and now U.S. Pat. No. 4,579,463, issued Apr. 1, 1986 filed simultaneously herewith.

Based on the foregoing principles, a highly sensitive method and apparatus can be developed for evaluating the surface conditions of a sample. In accordance with the subject invention, the apparatus includes a means for generating localized periodic heating at the surface of the sample. A light probe beam is then directed onto the surface of the sample within the area which has been periodically heated. A means is provided for detecting the intensity variations of the probe beam which has been reflected from the surface. As set forth above, only the variations which result from the periodic heating are revelant.

In one preferred embodiment, the sample is rastered relative to the heating and probe beams. Any changes in the output signal of the detector will indicate the presence of dopants or residues. In an alternate approach, the intensity variations measured can be compared to a known sample to evaluate the surface conditions.

Further objects and advantages of the subject invention will become apparent from the following detailed description taken in conjunction with the drawings in which:

BEST MODE FOR CARRYING OUT THE INVENTION

As described above, there is great interest in developing a method and apparatus for evaluating the surface conditions of a sample. As illustrated in FIGS. 1 and 2, one of the more pressing problems relates to the semiconductor industry and the detecting of residues produced during lithographic and etching processes. The importance of the problem is highlighted by the fact that even small amounts of residue left behind by either the lithography or etching process can lead to improperly functioning circuits. The difficulty of solving the problem can be appreciated when viewing FIGS. 1 and 2. As can be seen, the residues which must be detected lie in contacts or holes created on the substrate surface. These holes can have a width as small as 1 micron. Thus, any detecting technique must be capable of looking down into the holes, as indicated at arrows H1 and H2 in FIGS. 1 and 2, respectively. The subject invention overcomes these problems by providing a system which can be accurately focused into these holes to detect residues.

As set forth above, another problem relates to the evaluation of ion dopant concentrations at the surface of the sample as illustrated in FIG. 3. The subject invention provides a mechanism for solving both of these detection problems.

Figure 4:
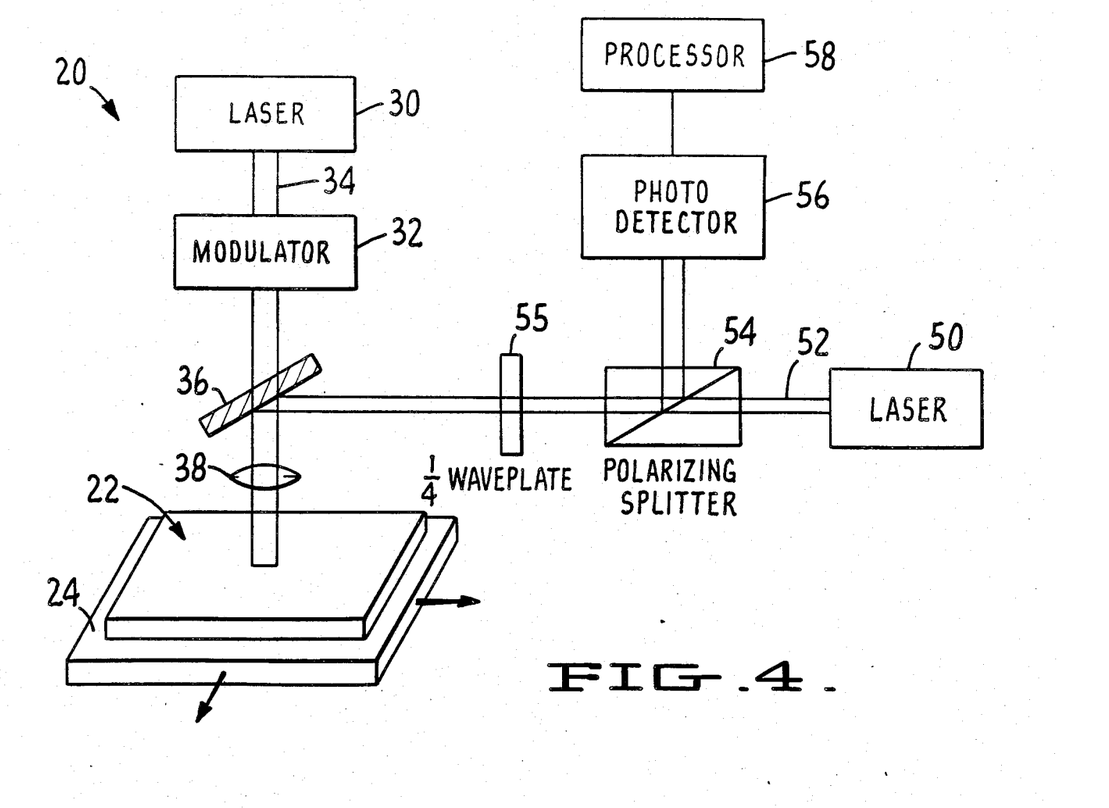
FIG. 4 is a composite block and schematic diagram of the apparatus for carrying out the detection of residues in accordance with the subject invention.

Referring now to FIG. 4, there is illustrated the appratus 20 for carrying out the method of the subject invention. In FIG. 4, a substrate 22 is shown which may be an integrated circuit or any other sample which needs to be evaluated. Sample 22 is shown resting on a platform 24 capable of rastering the sample with respect to the detecting apparatus. Controllable stages are well known in the art and are also disclosed in U.S. Pat. No. 4,255,971, cited above.

In accordance with the subject invention, the upper surface of the sample is subjected to a periodic localized heating. In the illustrated embodiment, this periodic localized heating is provided by a laser 30 which is intensity modulated by modulator 32. The frequency of modulation is based on the electronics but is preferably greater than 50 kHz.

The intensity modulated heating source could be supplied by electromagnetic radiation at various wavelengths, including X-rays, gamma rays, infrared, ultraviolet, visible light, microwaves or radio frequencies. The intensity modulated source can also be generated through thermal excitations arising from the interaction of the sample with an intensity modulated stream of particles, such as a beam of electrons, protons, neutrons, ions or molecules. However, because of the ability to focus a laser, it is believed that the illustrated embodiment is preferable.

The intensity modulated beam 34 is then passed through a dichroic mirror 36 and is preferably focused on a sample by a microscopic objective 38. In a preferred embodiment, the heating beam is an argon ion laser and the dichroic mirror is transparent to argon ion radiation. As will be discussed below, the dichroic mirror functions to reflect the probe laser beam, which is preferably generated by a helium-neon laser.

The periodic heating source disclosed above is identical to the type used in various thermal wave generation systems. In fact, the intensity modulated beam will function to generate thermal waves in the sample. As described in U.S. Pat. No. 4,255,971, cited above, information about the thermal conductivity of the uppermost layers of the sample can be determined by an analysis of the thermal waves generated in the sample. The reflectivity signal will be affected by the thermal parameters of the sample as set forth in equation (2). Thus, where the layer of interest is greater than 100 Angstroms thick, a component of the reflectivity signal $\Delta R_T$ will represent the thermal characteristics of the layer. In that case, information about the layer may be determined by an analysis of the thermal waves.

When the layer of interest is relatively thin, its thermal characteristics will not measurably affect the thermal parameters of the sample and thus will not measurably change the periodic surface temperature $\Delta T$. However, if the layer is at least 5 Angstroms thick, the layer will still alter the temperature coefficient of reflectivity ($\delta R/\delta T$) of the sample. The latter phenomenon is taken advantage of in the subject invention to permit the evaluation of extremely thin layers due to the change in the temperature coefficient of reflectivity.

In accordance with the subject invention, the detection means is defined by a light probe that emits a beam which is directed onto the surface of the sample that has been periodically heated by the modulated energy beam 34. In the illustrated embodiment, the light probe beam is generated by a helium-neon laser 50. Various other sources of electromagnetic radiation may be used for the probe beam as long as the beam reflectivity is affected by the temperature changes on the sample surface in a manner which can be measured. The probe beam 52 emanating from the helium-neon laser 50 is then passed through a polarizing splitter 54. The polarizing splitter is oriented in such a manner as to let the coherent light emanating from laser 50 to pass freely therethrough. The splitter will, however, deflect all light whose phase has been rotated through 90° relative to beam 52. The reason for this arrangement will become apparent below.

Light probe beam 52 is then passed through a $\frac{1}{8}\lambda$-waveplate 55. Waveplate 55 functions to rotate the phase of the beam by 45°. As can be appreciated, on the return path of the beam, the waveplate will rotate the phase of the beam another 45° so that when it reaches splitter 54, the phase of the beam has been rotated a total of 90° from the incoming orientation. By this arrangement, the splitter 54 will deflect the retro-reflected light beam up to detector 56, as discussed in more detail below.

After the probe beam 52 initially passes through the waveplate, it is reflected downwardly by dichroic mirror 36. As pointed out above, the dichroic mirror is transparent to argon ion light but will reflect the light rays in the helium-neon frequencies. In the preferred embodiment, the heating beam and the probe beam are aligned in a manner such that they are directed in a coincident manner down through lens 38 and focused at the same spot on the surface of the sample. By focusing the probe beam and the heating beam at the same spot, the maximum signal output can be achieved.

It is to be understood that the reflectivity signals of interest exist at any area on the surface of the sample which has been periodically heated by the beam 34. Therefore, the probe beam would not have to be directly coincident with the heating beam to detect the signals of interest. Accordingly, a microscope objective 38 is not necessary for focusing either the heating beam 34 or the probe beam 52. Rather, it is only necessary to direct the probe beam within at least a portion of the periodically heated area. A discussion and equations for calculating the size of the periodically heated area are set forth in copending application Ser. No. 401,511, and now U.S. Pat. No. 4,521,118, issued June 4, 1985 and incorporated herein by reference. Briefly, the diameter of the heated area, extending radially away from the center of the heating beam, is a function of the diameter and frequency of the heating beam and the thermal parameters in the sample.

Because the signals to be measured are so small, on the order of $10^{-5}$ of the D.C. level of the probe beam, every effort must be made to maximize the output for detection. Therefore, it would be desirable to direct the probe beam to be coincident with the heating beam. Movement of the beam may be accomplished by rotating mirror 36. In the preferred embodiment, where small "holes" or "contacts" are to be tested, the optical lens system should be capable of focusing the incoming heating and probe beams to a spot size of 1 micron in diameter.

The probe beam 52 impinges on the surface of the sample and interacts with the electrons and thus with the lattice structure of the sample. The lattice structure of the sample will undergo periodic changes as the temperature of the sample changes periodically. The probe beam essentially "sees" the changes in this lattice structure and the level of reflectivity of the beam changes along with the changing thermal conditions of the sample surface. The probe beam is reflected back up to the dichroic mirror where it is, in turn, reflected back along the incoming beam path through the $\frac{1}{8}\lambda$-waveplate 55. As discussed above, waveplate 55 rotates the phase of the probe beam by another 45° such that when the beam reaches splitter 54, its phase has been rotated 90° with respect to the original beam. Accordingly, the splitter will deflect the retro-reflected probe beam upwardly towards detector 56. Since intensity variations of the probe beam are to be detected, a standard photodetector may be employed as a sensing mechanism. The intensity variations which are measured are then supplied as an output signal to a processor 58 for evaluating the surface conditions of the sample.

Figure 5:
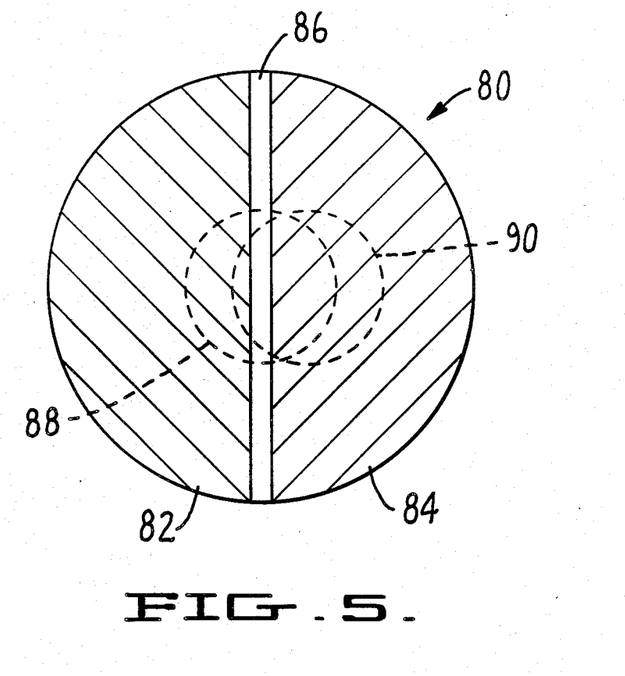
FIG. 5 is a bottom plan view of a typical split cell photodetector which may be utilized in the subject invention.

(1) FIG. 5 illustrates one type of standard photodetector 80 which is suitable for performing the intensity measurements of the subject invention. Photodetector 80 is referred to as a split cell detector and can be used not only to measure variations in intensity of the probe beam (shown in phantom at 88) due to changes in periodic reflectivity of the sample, but can also be used to measure changes in the angular displacement of the probe beam. Thermal wave measurement by detection of the angular changes in a probe beam is described in U.S. Pat. No. 4,521,118, cited above.

(2) Split cell detector 80 is defined by a photodetector having two sensing elements 82 and 84 located in a side-by-side arrangement separated by a divider 86 only a few microns thick. Each element 82, 84 generates an electrical signal proportional to the number of photons reaching that sector. Where the split cell is to be used to measure angular deviations of the probe beam, processor 58 functions to subtract the output of one sector from the output of the other. If, on the other hand, changes in reflectivity of the sample are to be measured, the output of elements 82 and 84 is summed.

(3) The sum of the signals of both segments gives a measure of the absolute value of the light energy falling on the photoconductor. As the total number of photons reflected from the sample surface changes in response to the changes in optical reflectivity of the sample, the summed output signal of the photodetector will change in proportion. This result is true even if the beam is experiencing angular displacements as shown in FIG. 5, due to the angular changes on the surface of the sample. Stated differently, even if the beam (shown in phantom at 90) is located off center of the photodetector, the sum of the two sides will still give a value of the total amount of energy reaching the surface of the photodetector. Thus, when the processor adds the output signals from the photodetector, the result will be independent of changes in the position of the probe beam.

(4) By analogy, the output of detector 80 (when measuring changes in reflectivity of the sample), will also be unaffected by the small changes in the diameter of the probe beam which may be induced by the periodic heating. As described in applicants' prior U.S. Pat. No. 4,522,510, issued June 11, 1985, periodic heating of a sample can create a periodically changing thermal lens in the sample. The presence of the thermal lens can be monitored by using a probe beam. For example, if a probe beam is passed, off-axis, through a periodically changing thermal lens, the beam will be periodically deflected. If the probe beam is passed through the center of thermal lens, its diameter will vary periodically by a small amount. The latter effect is described in U.S. Pat. No. 4,243,327, issued Jan. 6, 1981, to Frosch.

(5) The patent to Frosch describes a method for detecting the changes in diameter of a reflected probe beam induced by a changing thermal lens. This method is based on the principle that as the probe beam varies in diameter, the number of photons striking a fixed area having a diameter that is smaller than the probe beam diameter, will vary over time. Thus, the detector in Frosch is designed to measure the number of photons striking a particular area over time, that is, the areal density of the photons at the detector surface.

(6). In contrast, and as discussed above, in the subject device, the detector 56(80), in combination with processor 58, is arranged to measure the total amount of photons reflected from the sample, without regard to the location at which the photons impact on the detector or the areal density of those photons at the detector surface. In fact, since the output of detector 56 is proportional to the number of photons reflected from the sample surface, the resulting signals will be unaffected by the small changes in the beam diameter which may be induced by the periodic heating. Thus, on the subject device, the measurement of intensity changes of the reflected probe beam due to changes in reflectivity of the sample is independent of relatively small changes in both the position of the beam on the detector, as well as the diameter of the beam.

(7) As pointed out above, detector 56 (80) is arranged so that the total amount of power in the reflected probe beam is measured. This measurement could not be accomplished if any portion of the probe beam moved off the surface of the detector. As can be appreciated, if part of the probe beam misses the detector surface, the output signals therefrom would not be proportional to the total number of photons in the reflected probe beam. Therefore, it is necessary that the apparatus be arranged such that the diameter of the probe beam underfills, or is less than, the active surface of the photodetector (i.e. falls within its boundary), as shown in FIG. 5.

The operation of processor 58 is dependent on the type of testing configuration which is utilized. In all cases, however, the process is designed to evaluate the periodic intensity changes of the incoming probe beam which are the result of the reflectivity changes caused by the periodic heating on the sample. These high frequency changes are filtered to produce a signal which may be evaluated.

For simple spot testing, the processor may be programmed with the value of a known signal, for example, an uncoated or untreated oxide. If residues are present, as for example, as shown in hole H1 of FIG. 1, the output signal measured will be different from the known, stored signal, indicating the presence of residues. Because the identity of a particular residue is rarely known, an evaluation of the thickness of residue layer would be quite difficult. However, in most manufacturing situations, only the detection of the presence of the residue is necessary.

Another typical use for the subject system would be to evaluate an entire integrated circuit. In this case, a sample could be rastered with respect to the heating and probe beams. For example, the movements of platform 24 can be programmed in a manner to trace the paths defined by the etched tracks as shown in FIG. 2. If no residues remain, the output signal should remain constant. In contrast, any peaks or variations in the output signal will indicate the presence of residues.

With ion implanted dopants more quantitative information can be obtained because the identity, and thus the thermal characteristics, of both the substrate and the dopant are known. For example, the output signals can be normalized against a known reference sample such that actual concentrations of the implanted dopants may be obtained. As discussed above, this system is capable of detecting dopant levels prior to the annealing process. Unlike electrical testing, which requires the dopant to be activated, the ions locked at the interstitial sites, prior to annealing, will nonetheless affect the temperature coefficient of reflectivity and therefore can be monitored.

Furthermore, in practice, the subject invention has been shown to be capable of detecting boron ion dopant concentrations in silicon as low as $10^{10}$ ions/cm$^2$. This sensitivity is three orders of magnitude greater than the electrical testing available in the prior art. Analysis can also be performed by rastering the sample relative to the heating and probe beams to generate one or two dimensional maps of dopant concentrations.

In summary, there is provided a new and improved method and apparatus for evaluating the surface conditions of a sample. In accordance with the subject invention, a means is provided for generating a localized periodic heating at the surface of the sample. In the preferred embodiment, the heating means is an intensity modulated laser. The detection system further includes a probe beam which is focused on the area periodically heated by the intensity modulated laser in a manner to reflect off the surface of the sample. A means is provided for detecting the intensity variations of the reflected light resulting from the periodic heating. By processing the measured intensity variations of the reflected beam, surface conditions of the sample can be evaluated.

While the subject invention has been described with reference to a preferred embodiment, various other changes and modifications could be made therein, by one skilled in the art, without varying from the scope and spirit of the subject invention as defined by the appended claims.

We claim:

1. An apparatus for evaluating the surface conditions of a sample by measuring intensity variations of a reflected probe beam resulting from periodic changes in optical reflectivity of the sample induced by localized periodic heating, said apparatus comprising:

means for inducing a localized periodic heating at the surface of the sample;

a probe for emitting a beam of radiation;

means for directing the radiation probe beam within a portion of the area periodically heated by said periodic heating means in a manner such that the radiation probe beam reflects off the surface of the sample;

means for measuring the intensity variations of the reflected radiation probe beam resulting from the periodic changes in optical reflectivity of the sample induced by the periodic heating with the measured intensity changes being independent of changes in diameter or position of the probe beam; and means for processing the measured intensity variations of the reflected radiation probe beam resulting from the periodic changes in optical reflectivity of the sample to evaluate the surface conditions of the sample surface.

2. An apparatus as recited in claim 1 wherein said means for directing said radiation probe beam is arranged to direct said probe beam at the center of the area periodically heated by said periodic heating means.

3. An apparatus as recited in claim 1 where said periodic heating means is defined by an intensity modulated laser beam.

4. An apparatus as recited in claim 3 wherein said radiation probe beam is directed to be coincident with the heating laser beam.

5. An apparatus as recited in claim 4 further including a means for focusing said heating laser beam and said radiation probe to a spot size of 1 micron in diameter.

6. An apparatus as recited in claim 1 wherein said means for measuring the intensity variations of the reflected radiation probe beam is a photodetector.

7. An apparatus as recited in claim 1 wherein said processor means functions by comparing the intensity variations of the reflected radiation probe beam to those obtained from a known standard.

8. An apparatus as recited in claim 1 further including a means for rastering said sample relative to said heating means and said radiation probe beam wherein said processing means functions to compare intensity variations of the reflected radiation probe beam measured over the surface of the sample.

9. An apparatus as recited in claim 1 wherein said radiation probe is defined by a laser.

10. An apparatus as recited in claim 1 wherein said probe beam is directed to underfill the surface of the photodetector.

11. An apparatus for detecting residues on a sample by measuring intensity variations of a reflected probe beam resulting from periodic changes in optical reflectivity of the sample induced by localized periodic heating, said apparatus comprising:
means for inducing a localized periodic heating at the surface of the sample;
a probe for emitting a beam of radiation;
means for directing the radiation probe beam within a portion of the area periodically heated by said periodic heating means in a manner such that the radiation probe beam reflects off the surface of the sample;
means for measuring the intensity variations of the reflected radiation probe beam resulting from the periodic changes in optical reflectivity of the sample induced by the periodic heating with the measured intensity changes being independent of changes in diameter or position of the probe beam; and
means for processing the measured intensity variations of the reflected radiation probe beam resulting from the periodic changes in optical reflectivity of the sample to determine if residues are present on the sample surface.

12. An apparatus as recited in claim 11, wherein said means for directing said radiation probe beam is arranged to direct said probe beam at the center of the area periodically heated by said periodic heating means.

13. An apparatus as recited in claim 11, wherein said periodic heating means is defined by an intensity modulated laser beam.

14. An apparatus as recited in claim 13, further including a means for focusing said intensity modulated laser beam and said radiation probe beam in a coincident manner and to a spot size of 1 micron in diameter.

15. An apparatus as recited in claim 14 wherein said probe beam is directed to underfill the surface of the photodetector.

16. An apparatus for measuring dopant concentrations in a sample by measuring intensity variations of a reflected probe beam resulting from periodic changes in optical reflectivity of the sample induced by periodic heating, said apparatus comprising:
means for inducing a localized periodic heating at the surface of the sample;
a probe for emitting a beam of radiation;
means for directing the radiation probe beam within a portion of the area periodically heated by said periodic heating means in a manner such that the radiation probe beam reflects off the surface of the sample;
means for measuring the intensity variations of the reflected radiation probe beam resulting from the periodic changes in optical reflectivity of the sample induced by the periodic heating with the measured intensity changes being independent of changes in diameter or position of the probe beam; and
means for processing the measured intensity variations of the reflected radiation probe beam resulting from the periodic changes in optical reflectivity of the sample to evaluate the dopant concentrations in the sample.

17. An apparatus as recited in claim 16, wherein said means for directing said radiation probe beam is arranged to direct said probe beam at the center of the area periodically heated by said periodic heating means.

18. An apparatus as recited in claim 16, wherein said means for inducing the localized periodic heating is an intensity modulated laser beam.

19. An apparatus as recited in claim 16 wherein said probe beam is directed to underfill the surface of the photodetector.

20. A method for evaluating the surface conditions on a sample by measuring intensity variations of a reflected probe beam resulting from the periodic changes in optical reflectivity of the sample induced by localized periodic heating, said method comprising the steps of:
inducing a periodic localized heating on the surface of the sample;
directing a radiation beam within a portion of the area periodically heated by the periodic heat source in a manner such that the radiation beam reflects from the surface of the sample;
measuring the intensity variations of the reflected radiation beam resulting from said periodic changes in optical reflectivity of the sample induced by said periodic heating with the measured intensity changes being independent of changes in diameter or position of the probe beam; and
processing the measured intensity variations of the reflected radiation beam resulting from the periodic changes in optical reflectivity of the sample to evaluate the conditions of the sample surface.

21. A method as recited in claim 16 wherein said radiation beam is directed at the center of the periodically heated area on the sample surface.

22. A method as recited in claim 16 wherein said processing step is carried out by comparing the intensity variations of the reflected radiation beam to those obtained from a known standard.

23. A method as recited in claim 16 further including the step of rastering the sample relative to the periodic heat source wherein said processing step includes comparing the intensity variations of the reflected radiation beam measured over the surface of the sample.

24. A method for detecting residues on a sample by measuring intensity variations of a reflected probe beam resulting from the periodic changes in optical reflectivity of the sample induced by localized periodic heating, said method comprising the steps of:

inducing a periodic localized heating on the surface of the sample;

directing a radiation beam within a portion of the area periodically heated by the periodic heat source in a manner such that the radiation beam reflects from the surface of the sample;

measuring the intensity variations of the reflected radiation beam resulting from said periodic changes in optical reflectivity of the sample induced by said periodic heating with the measured intensity changes being independent of changes in diameter or position of the probe beam; and processing the measured intensity variations of the reflected radiation beam resulting from the periodic changes in optical reflectivity of the sample to determine if residues are present on the sample surface.

25. A method as recited in claim 24 wherein said radiation beam is directed at the center of the periodically heated area on the surface of the sample.

26. A method for measuring dopant concentrations in a sample by measuring intensity variations of a reflected probe beam resulting from the periodic changes in optical reflectivity of the sample induced by localized periodic heating, said method comprising the steps of:

inducing a periodic localized heating on the surface of the sample;

directing a radiation beam within a portion of the area periodically heated by the periodic heat source in a manner such that the radiation beam reflects from the surface of the sample;

measuring the intensity variations of the reflected radiation beam resulting from said periodic changes in optical reflectivity of the sample induced by said periodic heating with the measured intensity changes being independent of changes in diameter or position of the probe beam; and processing the measured intensity variations of the reflected radiation beam resulting from the periodic changes in optical reflectivity of the sample to evaluate the dopant concentrations in the sample.

27. A method as recited in claim 26 wherein said radiation beam is directed at the center of the periodically heated area on the sample surface.

* * * * *

UNITED STATES PATENT AND TRADEMARK OFFICE
CERTIFICATE OF CORRECTION

PATENT NO. : 4,636,088
DATED : January 13, 1987
INVENTOR(S) : Allan Rosencwaig and Walter L. Smith It is certified that error appears in the above-identified patent and that said Letters Patent is hereby corrected as shown below:

Column 12, line 60, change the dependency of claim 21 from "claim 16" to --claim 20--.

Column 12, line 63, change the dependency of claim 22 from "claim 16" to --claim 20--.

Column 12, line 67, change the dependency of claim 23 from "claim 16" to --claim 20--.

Signed and Sealed this

Twenty-fourth Day of March, 1998

Attest:

BRUCE LEHMAN

*Attesting Officer*        *Commissioner of Patents and Trademarks*